US00PP16923P2

(12) United States Plant Patent
Schweizer

(10) Patent No.: US PP16,923 P2
(45) Date of Patent: Aug. 1, 2006

(54) ***COREOPSIS* PLANT NAMED 'LIMEROCK DREAM'**

(50) Latin Name: *Coreopsis hybrida*
Varietal Denomination: Limerock Dream

(75) Inventor: Pamela S. Schweizer, Lancaster, PA (US)

(73) Assignee: Limerock Plant Farm, Inc., Lincoln, RI (US)

( * ) Notice: Subject to any disclaimer, the term of this patent is extended or adjusted under 35 U.S.C. 154(b) by 0 days.

(21) Appl. No.: 11/141,557

(22) Filed: May 31, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Coreopsis* plant named 'Limerock Dream', characterized by its daisy-type inflorescences that are about 3 cm in diameter; unique yellow orange and red purple-colored ray florets; very freely flowering with numerous inflorescences per plant; upright and outwardly spreading growth habit; and freely branching growth habit.

1 Drawing Sheet

Botanical designation: *Coreopsis hybrida.*
Cultivar denomination: 'Limerock Dream'.

BACKGROUND OF THE INVENTION

The present invention relates to a new and distinct cultivar of *Coreopsis* plant, botanically known as *Coreopsis hybrida* and hereinafter referred to by the name 'Limerock Dream'.

The new *Coreopsis* was discovered and selected by the Inventor in a controlled environment in Smoketown, Pa. in May, 2004, as a naturally-occurring whole plant mutation of the *Coreopsis hybrida* cultivar Limerock Passion, disclosed in U.S. Plant Pat. No. 15,979. The whole plant mutation was observed by the Inventor within a population of flowering plants of the cultivar Limerock Passion.

Asexual reproduction of the new *Coreopsis* by vegetative tip cuttings in a controlled environment in Smoketown, Pa., since August, 2004, has shown that the unique features of this new *Coreopsis* are stable and reproduced true to type in successive generations.

SUMMARY OF THE INVENTION

The cultivar Limerock Dream has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Limerock Dream'. These characteristics in combination distinguish 'Limerock Dream' as a new and distinct cultivar:

1. Daisy-type inflorescences that are about 3 cm in diameter.
2. Unique yellow orange and red purple-colored ray florets.
3. Very freely flowering with numerous inflorescences per plant.

4. Upright and outwardly spreading growth habit.
5. Freely branching growth habit; dense and bushy plants.

Plants of the new *Coreopsis* are most similar to plants of the parent, the cultivar Limerock Passion. In side-by-side comparisons conducted in Smoketown, Pa., plants of the new *Coreopsis* differed primarily from plants of the cultivar Limerock Passion in ray floret coloration as plants of the cultivar Limerock Passion have light red purple-colored ray florets.

Plants of new *Coreopsis* can also be compared to plants of the cultivar Limerock Ruby, disclosed in U.S. Plant Pat. No. 15,455. In side-by-side comparisons conducted in Smoketown, Pa., plants of the new *Coreopsis* differed primarily from plants of the cultivar Limerock Ruby in ray floret coloration as plants of the cultivar Limerock Ruby have dark crimson red-colored ray florets.

BRIEF DESCRIPTION OF THE PHOTOGRAPH

The accompanying colored photograph illustrates the overall appearance of the new *Coreopsis*, showing the colors as true as it is reasonably possible to obtain in colored reproductions of this type. Colors in the photograph may differ slightly from the color values cited in the detailed botanical description which accurately describe the colors of the new *Coreopsis*. The photograph is a close-up view of typical inflorescences of 'Tangerine Dream'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Smoketown, Pa. during the summer and fall in a polyethylene-covered greenhouse and under cultural conditions which approximate commercial practice. During the production of the plants, day temperatures ranged from 21 to 46° C. and night temperatures ranged from 18 to 29° C. Plants used for the photographs and description were grown for about one year in one-gallon containers.

Botanical classification: *Coreopsis hybrida* cultivar Limerock Dream.

Parentage: Naturally-occurring whole plant mutation of *Coreopsis hybrida* cultivar Limerock Passion, disclosed in U.S. Plant Pat. No. 15,979.

Propagation:

*Type.*—Vegetative tip cuttings.

*Time to initiate roots.*—Summer: About 18 days at temperatures of 18° C. Winter: About 20 days at temperatures of 13° C.

*Time to produce a rooted cutting.*—About 36 days at temperatures of 13 to 18° C.

*Root description.*—Fine; well-branched.

Plant description:

*Appearance.*—Perennial; upright and outwardly spreading; mounding habit.

*Plant height.*—About 26.5 cm.

*Plant diameter or spread.*—About 28.5 cm.

*Branching habit.*—Freely branching habit; usually two laterals will develop at every node. Pinching is typically not required.

*Lateral branch description.*—Aspect: Initially upright, then outwardly spreading. Strength: Moderately strong. Length: About 16.5 cm. Diameter: About 2 mm. Internode length: About 2.6 cm. Texture: Smooth, glabrous. Color: Close to 146A.

*Foliage description.*—Arrangement: Opposite, single or trifoliate; sessile. Single leaf length: About 3.2 cm. Terminal leaflet length: About 3.5 cm. Lateral leaflet length: About 2 cm. Single leaf width: About 2.5 mm. Terminal leaflet width: About 3.5 mm. Lateral leaflet width: About 2 mm. Shape: Linear; narrow. Apex: Acute. Base: Attenuate. Texture, upper and lower surfaces: Smooth, glabrous. Color: Developing foliage, upper surface: Close to 147A. Developing foliage, lower surface: Close to 146A. Fully expanded foliage, upper surface: More green than 147A; venation, similar to lamina. Fully expanded foliage, lower surface: 147A to 146A; venation, similar to lamina.

Flowering description:

*Appearance.*—Daisy-type inflorescence form with elongated oblong to broadly linear-shaped ray florets. Inflorescences borne on terminals, arising from leaf axils. Disc and ray florets develop acropetally on a capitulum. Inflorescences persistent.

*Flowering response.*—Under natural conditions, plant flower in the late spring after sufficient cool temperatures and continue to flower through the fall.

*Inflorescence longevity.*—Individual inflorescences last about one to two weeks.

*Quantity of inflorescences.*—Very freely flowering with about 15 inflorescence buds and inflorescences per lateral branch.

*Inflorescence size.*—Diameter: About 3 cm. Depth (height): About 7.5 mm. Diameter of disc: About 5.5 mm. Receptacle diameter: About 3 mm.

*Fragrance.*—Very faint; sweet, grass-like.

*Inflorescence buds.*—Height: About 5 mm. Diameter: About 3.5 mm. Shape: Ovoid. Color: Close to 146A overlain with close to 187A.

*Ray florets.*—Shape: Elongated oblong to broadly linear. Length: About 1.5 cm. Corolla tube length: About 2.5 mm. Width: About 7 mm. Corolla tube diameter: About 1 mm. Apex: Emarginate; deeply incised; jagged appearance. Base: Attenuate. Margin: Entire. Texture: Smooth, glabrous; satiny. Aspect: Initially upright; with development, perpendicular to the peduncle; mostly flat. Number of ray florets per inflorescence: About seven or eight arranged in a single whorl. Color: When opening and fully opened, upper surface: Close to 9A to 12A to 15A; towards the apex, overlain with longitudinal streaks, close to 53A. When opening and fully opened, lower surface: Close to 9C to 9D; towards the apex, underlain with longitudinal streaks, close to 59A.

*Disc florets.*—Arrangement: Massed at the center of the inflorescence. Shape: Tubular, flared at apex. Length: About 3.5 mm. Width: Apex: About 1 mm. Base: Less than 1 mm. Number of disc florets per inflorescence: About 24. Color, immature and mature: Apex: Close to 187A. Mid-section: Close to 12A. Base: Close to 150D.

*Involucral bracts.*—Quantity: About eight arranged in a single whorl. Length: About 5 mm. Width: About 3 mm at the base. Shape: Elongated oblong. Apex: Acute. Base: Truncate, fused. Texture, upper and lower surfaces: Smooth, glabrous; waxy. Color, upper and lower surfaces: Towards the base, close to 146A; towards the apex, close to 146A overlain with close to 169A; at the apex, close to 187A.

*Pappus.*—Length: About 5 mm. Width: About 1 mm. Color: Close to 169A.

*Peduncle.*—Strength: Very strong, wiry; flexible. Aspect: Upright to about 45° from vertical. Length: About 3.4 cm. Diameter: Less than 1 mm. Texture: Smooth, glabrous. Color: Close to 146A.

*Reproductive organs.*—Androecium: Present on disc florets only. Stamen quantity: Five per floret. Anther length: About 1 mm. Anther color: 187A to 202A. Amount of pollen: Scarce. Pollen color: Close to 21A. Gynoecium: Present on disc florets only. Pistil quantity: One per floret. Pistil length: About 3 mm. Stigma shape: Bi-parted. Stigma color: Close to 21A. Style color: Close to 155A.

*Seed/fruit.*—Seed/fruit production has not been observed.

Disease/pest resistance: Resistance to pathogens and pests common to *Coreopsis* has not been observed on plants grown under commercial conditions.

Temperature tolerance: Plants of the new *Coreopsis* have demonstrated good tolerance to night temperatures as low as −5° C. and day temperatures as high as 50° C.

It is claimed:

1. A new and distinct cultivar of *Coreopsis* plant named 'Limerock Dream', as illustrated and described.

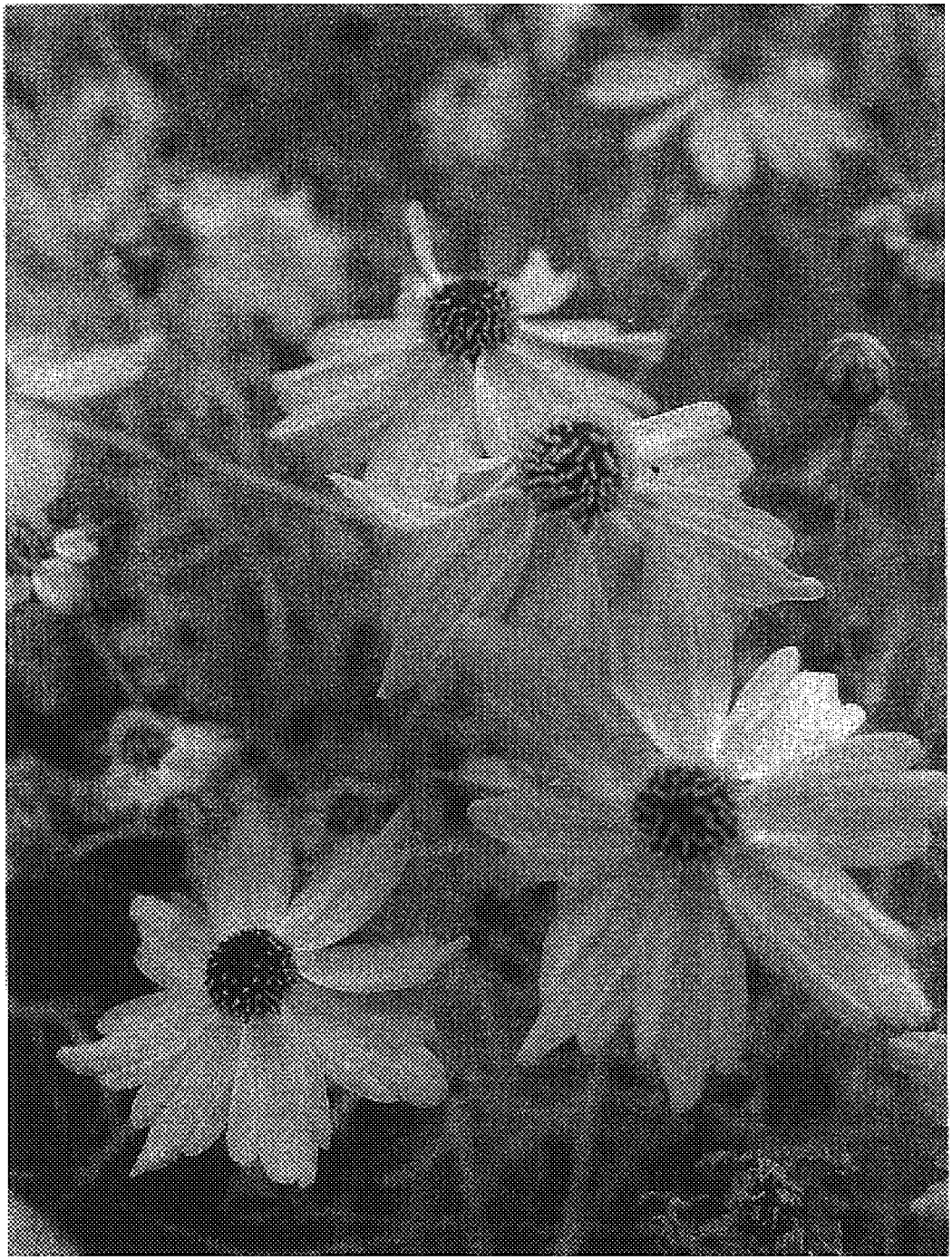

* * * * *